United States Patent [19]

Kijima et al.

[11] Patent Number: 5,192,325

[45] Date of Patent: Mar. 9, 1993

[54] CERAMIC IMPLANT

[75] Inventors: Naoto Kijima, Yokohama; Yasuo Oguri, Tokyo, both of Japan

[73] Assignee: Mitsubishi Kasei Corporation, Tokyo, Japan

[21] Appl. No.: 903,327

[22] Filed: Jun. 24, 1992

Related U.S. Application Data

[62] Division of Ser. No. 596,954, Oct. 15, 1990, which is a division of Ser. No. 307,640, Feb. 8, 1989, Pat. No. 4,983,182.

[30] Foreign Application Priority Data

| Feb. 8, 1988 | [JP] | Japan | 63-27027 |
| Feb. 8, 1988 | [JP] | Japan | 63-27029 |
| Feb. 8, 1988 | [JP] | Japan | 63-27031 |

[51] Int. Cl.$^5$ ............................................. A61F 2/28
[52] U.S. Cl. ..................................... 623/16; 433/201.1
[58] Field of Search ................. 623/16, 18, 23, 66; 433/201.1

[56] References Cited

U.S. PATENT DOCUMENTS

| 4,308,064 | 12/1951 | Tukam et al. | 501/135 |
| 4,626,392 | 12/1986 | Kondo et al. | 623/16 |
| 4,636,218 | 1/1987 | Fukuuara et al. | 623/16 |
| 4,722,915 | 7/1988 | Somi et al. | 501/103 |
| 4,740,288 | 4/1988 | Yunido | 504/412 |
| 4,771,950 | 4/1988 | Coblenz et al. | 241/1 |
| 4,882,146 | 11/1989 | Shmomane et al. | 427/2 |
| 4,950,294 | 8/1990 | Hakamatsuka | 623/16 |
| 4,957,509 | 9/1990 | Tamani et al. | 623/16 |
| 4,969,913 | 11/1990 | Ojimo | 623/66 |
| 4,983,182 | 1/1991 | Kijma et al. | 623/18 |
| 5,064,436 | 11/1991 | Ogiso et al. | 623/16 |

Primary Examiner—David Isabella
Attorney, Agent, or Firm—Oblon, Spivak, McClelland, Maier & Neustadt

[57] ABSTRACT

A ceramic implant comprising a sintered body of zirconia and a coating layer of a porous sintered body of a mixture comprising α-tricalcium phosphate and zirconia, or hydroxyapatite and zirconia formed on the surface of the sintered body of zirconia.

7 Claims, No Drawings

CERAMIC IMPLANT

This application is a divisional of copending application Ser. No. 07/596,954, filed Oct. 15, 1990, which is a divisional of Ser. No. 07/307,640, filed Feb. 8, 1989, now U.S. Pat. No. 4,983,182.

The present invention relates to a ceramic implant comprising a sintered body of zirconia and a coating layer of a porous sintered body of a mixture comprising α-tricalcium phosphate (hereinafter referred simply as α-TCP) and zirconia, or hydroxyapatite (hereinafter referred to simply as HAP) and zirconia, formed on the surface of the sintered body of zirconia, and a process for its production.

As implant material for hard tissue in a living body, such as an artificial tooth root, metals such as stainless steel alloy and titanium alloy, ceramics such as single crystal alumina, a sintered body of alumina, a sintered body of zirconia and carbon, are mainly employed. These materials are called biologically inactive implant materials, since they do not directly bond to vital tissue. On the other hand, a sintered body of HAP, a sintered body of α-TCP and a sintered body of β-tricalcium phosphate are so-called biologically active implant materials, and they have attracted an attention as materials capable of directly chemically bonding to vital tissue. In recent years, attemps have been made to coat a biologically active substance on the surface of a biologically inactive material by plasma spray coating.

In a case where the biologically inactive implant material is used as embedded in a living body, it is incapable of directly bonding to the vital tissue, and loosening occurs during the use for a long period of time. On the other hand, the biologically active implant material is free from such loosening, but it is inferior in the mechanical strength to the biologically inactive material, and it tends to be broken during the use in a living body. The product obtained by coating a biologically active substance on the surface of a biologically inactive material by plasma spray coating, is likely to undergo peeling since the adhesion between the core material and the surface layer formed by the plasma spray coating is weak.

The present inventors have conducted extensive researches in view of the above problems. As a result, they have found that a ceramic implant having a coating layer of a porous sintered body of a mixture of α-TCP and zirconia, or hydroxy apatite and zirconia, on the surface of a sintered body of zirconia, has high mechanical strength and is free from breakage in a living body, and the biologically active surface porous layer bonded firmly to the core material, is capable of bonding to vital tissue in the living body, whereby it can be a material durable for use for a long period of time. The present invention has been accomplished on the basis of this discovery.

The present invention provides a ceramic implant comprising a sintered body of zirconia and a coating layer of a porous sintered body of a mixture comprising α-TCP and zirconia, or HAP and zirconia, on the surface of the sintered body of zirconia.

Further, the present invention provides a process for producing a ceramic implant, which comprises coating a powder mixture comprising hydroxy apatite and zirconia on the surface of a molded product of partially stabilized zirconia, followed by sintering and, if necessary, by subsequent hydrothermal treatment.

The present invention is particularly suitable as a base material for the above-mentioned implant, but it includes a sintered zirconia shaped product useful and excellent and capable of being used for other applications, and a process for its production.

Namely, a sintered body of zirconia is usually obtained by sintering a shaped product of zirconia molded by various molding methods such as dry-pressing, extrusion, slip-casting, injection-molding and tape-casting. In a case where a sintered body of zirconia having a complicated shape is to be produced, slip-casting or injection-molding is selected from the above-mentioned molding methods. Slip-casting is considered to be most useful when sintered bodies of zirconia having complicated shapes are produced in a small quantity and in various different types, and it is practically used on an industrial scale.

However, sintered bodies of zirconia obtained by slip-casting are usually inferior in the density and flexural strength to sintered bodies of zirconia obtained by dry-pressing, and they have an additional problem of poor dimensional stability since the heat shrinkage of the shaped product during drying or sintering is substantial, and they are susceptible to deformation.

The present inventors have conducted various studies on these points. As a result, they have found it possible to obtain a sintered product of zirconia having high density and flexural strength and excellent dimensional stability when a partially stabilized zirconia slurry is prepared under a certain condition, followed by slip-casting and sintering.

Namely, on the basis of this discovery, the present invention provides a process for producing a sintered body of zirconia, which comprises subjecting partially stabilized zirconia powder to wet pulverization treatment in the presence of water and a dispersant, and slip-casting the resulting slurry, followed by sintering, wherein as the partially stabilized zirconia powder, a powder having a BET specific surface area of from 5 to 10 $m^2/g$ is employed, and the wet pulverization treatment is conducted so that the BET specific surface area of the partially stabilized zirconia powder increases from 1.05 to 2.0 times relative to the starting material.

Now, the present invention will be described in detail.

The partially stabilized zirconia powder used in the present invention is a zirconia powder having CaO, MgO, $Y_2O_3$, $Gd_2O_3$ or $CeO_2$ solid-solubilized as a stabilizing agent. It is preferably a powder having a BET specific surface area of from 5 to 10 $m^2/1$ g to obtain a sintered product having high density and strength and good dimensional stability. If the specific surface area of the powder is less than 5 $m^2/g$, the sintering of the powder tends to be difficult, and the density and strength tend to be poor. On the other hand, if the specific surface area of the powder is larger than 10 $m^2/g$, the packing density of zirconia particles constituting the shaped product after slip-casting, tends to be small, and the heat shrinkage during the sintering tends to be substantial, whereby the dimensional stability tends to be poor. Further, the shaped product immediately after the molding tends to undergo distortion, and cracking is likely to take place when dried.

The wet pulverization treatment is preferably conducted so that the BET specific surface area of the partially stabilized zirconia powder increases from 1.0 to 2.0 times relative to the starting material. The partially stabilized zirconia having a specific surface area of from 5 to 10 m²/g is prepared by presintering and contains a substantial amount of coarse aggromerates of firmly bonded primary particles. If the partially stabilized zirconia powder after the wet pulverization treatment is pulverized so that the BET specific surface area becomes at least 1.05 times relative to the starting material, the coarse aggromerates can be removed to a substantial extent. However, if the pulverization treatment is conducted so much that the BET specific surface area exceeds 2.0 times, the packing density of zirconia particles in the shaped product after slip-casting tends to be small, whereby the dimensional stability after sintering tends to be poor, and the shaped product immediately after the molding tends to undergo a distortion and cracking is likely to take place during the drying step.

The zirconia slurry concentration during the wet pulverization treatment may be at any level so long as a slurry condition is obtained where the partially stabilized zirconia powder is uniformly dispersed in water in the presence of water and a dispersant. However, it is preferred to conduct the wet pulverization treatment under a slurry concentration where the weight ratio of the partially stabilized zirconia to the total weight of water and the partially stabilized zirconia, is from 75 to 90% by weight. If the slurry concentration is too low, the pulverization efficiency tends to be low, and if the slurry concentration is too high, it tends to be difficult to maintain the slurry condition.

The amount of the dispersant to be used for the wet pulverization treatment, may be at any level so long as it is capable of imparting good fluidity to the slurry. However, it is preferably from 0.1 to 1.0% by weight relative to the partially stabilized zirconia. If the amount of the dispersant is too small, the thixotropic properties of the slurry become substantial, whereby it becomes difficult to control the wall thickness in the slip-casting. On the other hand, if the amount of the dispersant is too much, the viscosity of the slurry becomes so high that it becomes difficult to inject or discharge the slurry during the slip-casting, and orgnaic substances contained in the dispersant and the sodium and phosphorus contents will be substantial, whereby cracking is likely to take place during the sintering, and the sodium and phosphorus elements will remain in the sintered product to deteriorate the physical properties of the sintered product.

The dispersant may be of any type so long as it is capable of dispersing the partially stabilized zirconia powder in water and reducing the slurry viscosity. However, it is preferably an ammonium salt of an acrylate polymer composed essentially of acrylic acid. An inorganic dispersant such as sodium hexametaphosphate provides excellent dispersing effects with a very small amount, but it remains as an inorganic impurity in the sintered body of zirconia after sintering and tends to deteriorate the physical properties of the sintered product. Further, many organic dispersants are poor in the dispersing performance. Polyammonium acrylate exhibiting the best dispersing performance among organic dispersants, has a dispersing performance at the same level as the inorganic dispersant.

The pH during the wet pulverization treatment is preferably from 9 to 10. The partially stabilized zirconia powder takes the largest absolute value of ξ-potential in water having a pH within this range, whereby a slurry in an excellently dispersed state can be obtained. If the pH of the slurry shifts to the acidic side, there will be a problem that $Y^{3+}$ ions elute from the surface of the partially stabilized zirconia powder as the pulverization treatment proceeds. On the other hand, if the pH shifts to the strongly alkaline side or to a strongly acidic side, a gypsum mold commonly employed as an inexpensive mold for slip-casting will be dissolved, whereby the useful life of the mold will be shortened.

As the wet pulverization treatment system, it is preferred to employ a pulverization treatment system wherein balls are used as pulverizing means. Particularly preferred is two step treatment of slurrying by means of a vibration ball mill, followed by treatment by means of a rotary ball mill. The vibration ball mill has high pulverization and mixing efficiency, whereby the powder surface will be uniformly wetted with water and the dispersant in a relatively short period of time to obtain a slurry. However, if the vibration ball mill is used alone, it will be difficult to remove coarse aggregates. On the other hand, the rotary ball mill is suitable for removing such coarse aggregates. Accordingly, if the two step treatment comprising slurrying by means of the vibration ball mill and subsequent treatment by the rotary ball mill, the slurrying can be carried out in a short period of time, and coarse aggregates can easily be removed.

The shaped product of the partially stabilized zirconia powder can be obtained by various molding methods such as dry-pressing, extrusion, slip-casting, injection-molding and tape-casting. However, it is preferred to employ slip-casting or injection-molding which is capable of producing a shaped product having a complicated shape.

The shaped product of zirconia thus prepared has high strength and reliability and also has excellent dimensional stability. Namely, by the above-mentioned process, it is possible to obtain a sintered body having a flexural strength of at least 100 kgf/mm² and a Weibull coefficient of at least 10, more preferably a flexural strength of 120 kgf/mm² and a Weibull coefficient of at least 15. Here, the Weibull coefficient is a constant given by the value m in the formula:

$$\ln\ln\left(\frac{1}{1-f}\right) = m l_n \sigma_r + m l_n\left[\frac{\Gamma\{(m+1)/m\}}{\mu}\right]$$

wherein f is the probability of breakage, $\sigma_r$ is the strength at the time of the breakage of each test sample, and $\mu$ is an average strength, and it represents reliability. Accordingly, high strength and high Weibull coefficient as in the present invention, mean that products of high strength can be obtained in high reliability e.g. with little fractuation, such being particularly desirable for a material to be used as an implant designed to be embedded in a living body.

Various methods may be available for providing a coating layer of a porous sintered body of a mixture comprising α-TCP and zirconia, or HAP and zirconia, on the surface of the sintered body of zirconia. Most preferably, zirconia powder and HAP are coated on the surface of a non-sintered shaped body of zirconia, followed by sintering, whereby HAP will be converted to α-TCP, and the non-sintered shaped body of zirconia will be sintered. If the product is subjected to hydrothermal treatment, α-TCP is reconverted to HAP to obtain a coating layer of a mixture of HAP and zirconia. Thus, the coating layer is formed on the sintered product of zirconia.

As HAP powder, a powder represented by the chemical formula $Ca_{10-x}(HPO_4)_x(PO_4)_{6-x}(OH)_{2-x} \cdot nH_2O$ wherein $0 \leq x \leq 1$ may be mentioned.

The zirconia powder to be mixed with HAP may be any powder composed essentially of zirconia irrespective of whether or not it contains a stabilizing agent.

With respect to the mixing ratio of HAP and zirconia, the weight ratio of zirconia to HAP is selected within a range of from 0.05 to 20. More preferably, they are mixed so that the above ratio is within a range of from 0.1 to 2.5. If the weight ratio of zirconia to HAP is less than 0.05, the porosity of the coating layer of the resulting implant tends to be small, whereby the biological activity will be small, and a number of cracks will be formed at the surface of the coating layer or at the interface between the sintered body of zirconia and the coating layer during the cooling after the sintering, due to a substantial difference in the thermal expansion coefficient between the sintered body of zirconia as the, core material and the coating layer. On the other hand, if the weight ratio of zirconia to HAP exceeds 20, the porosity of the coating layer of the resulting implant tends to be small, and the content of $\alpha$-TCP will be reduced, whereby the biological activity tends to be low.

As a method for coating a powder mixture of HAP and zirconia on the surface of a shaped body of the partially stabilized zirconia, a method is employed which is capable of uniformly coating the powder mixture on the surface of the shaped product. Specifically, a method is employed wherein a powder mixture of HAP and zirconia is uniformly dispersed in water to obtain a slurry, and a shaped product of the partially stabilized zirconia is immersed in this slurry so that water in the slurry will be absorbed in the shaped product and at the same time, the powder mixture will be coated uniformly on the surface of the shaped product. A similar coating is possible by spraying the above-mentioned slurry to the shaped product.

The sintering is conducted within a temperature range of from 1,200° to 1,550° C. If the temperature is too low, the density and strength of the sintered product of zirconia tend to be low. On the other hand, if the temperature is too high, the porosity of the porous sintered body of a mixture of $\alpha$-TCP and zirconia, tends to be low, and the formed $\alpha$-TCP will be melted. Further, if the temperature is too high, abnormal grain growth of zirconia takes place, whereby the density of the sintered body of zirconia tends to be low, and at the same time, the content of monoclinic zirconia not contributing to the strength of the sintered body of zirconia tends to be high, whereby the strength will likely be low. Namely, by conducting the sintering within a proper temperature range, it is possible not only to increase the density and strength of the sintered body of zirconia as the core material of an implant, but also to increase the porosity of the porous sintered body as the coating layer of the implant.

By this sintering, $\alpha$-TCP resulting from HAP and zirconia, will firmly bond to each other while maintaining the porosity, and firm bonding is also formed between the sintered body of zirconia as the core material and the porous sintered body. This is believed to be attributable to the transfer and diffusion of $Ca^{2+}$ ions in HAP to the zirconia powder and to the core material zirconia.

Further, the products may be subjected to hydrothermal treatment to convert $\alpha$-TCP again to HAP.

Such hydrothermal treatment is preferably conducted within a temperature range of from 60° to 300° C. If the temperature is too low, the reaction time for the conversion of $\alpha$-TCP to HAP will be very long. If the temperature is too high, the apparatus will be expensive, such being unsuitable from the industrial point of view.

The time required for the hydrothermal treatment is usually from 10 minutes to 50 hours. If the treating time is too short, only the surface of $\alpha$-TCP will be converted to HAP, and the conversion of $\alpha$-TCP to HAP will be incomplete. On the other hand, if the treating time is too long, the surface of the sintered body of zirconia undergoes a phase transfer from tetragonal zirconia to monoclinic zirconia. If this phase transfer progresses, cracks will form on the surface, whereby the strength will be low. Particularly within a temperature range of from 150° to 250° C., the phase transfer rate is high, and the treating time should be shortened.

Now, the present invention will be described in further detail with reference to Examples. However, it should be understood that the present invention is by no means restricted to such specific Examples.

EXAMPLE 1

Into a ball mill pot made of alumina having an internal capacity of 250 ml, 30.3 g of distilled water and 0.35 g of an aqueous solution containing 40% by weight of ammonium polyacrylate as a dispersant, were introduced and mixed, and then 93.4 g of partially stabilized zirconia powder containing 5.46% by weight of $Y_2O_3$ and having a BET specific surface area of 6.0 $m^2/g$ and 400 g of zirconia balls having a diameter of 10 mm were added thereto. The mixture was introduced to a vibration ball mill and subjected to wet pulverization treatment for one hour, and further to wet pulverization treatment in a rotary ball mill for 24 hours to obtain a zirconia slurry. The slurry concentration was 75.4% by weight, and the dispersant was used in an amount of 0.15% by weight relative to the partially stabilized zirconia, and the pH of the slurry was 9.90. The apparent viscosity of the slurry was 0.17 poise at a shear rate of 10 $sec^{-1}$. A part of the slurry was dried and heated at 500° C. for one hour to remove water and ammonia polyacrylate from the partially stabilized zirconia powder, whereupon the BET specific surface area of the powder was 6.8 $m^2/g$, which is 1.13 times relative to the starting material powder. To 117.5 g of the rest of the slurry, 1.05 g of a binder in a 42 wt % aqueous solution and 0.044 g of a defoaming agent were added thereto. The mixture was stirred for 30 minutes, and the resulting slurry was subjected to defoaming under reduced pressure of 20 Torr for 20 minutes in a rotary evaporator. The slurry concentration at that time was 75% by weight, and the pH of the slurry was 9.71. The apparent viscosity of the slurry was 0.18 poise at a shear rate of 10 $sec^{-1}$. This slurry was subjected to slip-casting in a gypsum mold having an internal dimension of 55.4 mm × 55.4 mm × 5.0 mm at room temperature of 25° C. In about 30 minutes, the wall formation was completed, and about 150 minutes later, the slip-casted product was taken out from the mold. The molded product was dried at 25° C. for one day and at 90° C. for one day. Then, the dried product was heated in an electric furnace to 500° C. at a rate of 10° C./hr and maintained at 500° C. for one hour for degreasing. Then, the temperature was raised at a rate of 200° C./hr, and sintering was conducted at 1,500° C. for 2 hours. The sintered product thus obtained had a dimension of 45.1 mm×45.1 mm×4.2 mm. Thus, the heat shrinkage was 18.6% from the cast body and 16.7% from the dried slip-casted product. No deformation or crack was observed on this sintered product, and the density was 6.01 g/cm³. The flexural strength was measured in accordance with JIS R1601, whereby the average strength was 118 kgf/mm², and the Weibull coefficient was 30.

EXAMPLES 2 to 11

Sintered bodies of zirconia were prepared in the same manner as in Example 1 under the conditions as identified in Table 1. The results are shown in Table 1 together with the results of Example 1.

COMPARATIVE EXAMPLE 1

Into a ball mill pot made of alumina having an internal capacity of 250 ml, 58.9 g of distilled water and 1.8 g of an aqueous solution containing 40% by weight of ammonium polyacrylate as a dispersant, were charged and mixed. Then, 180.0 g of partially stabilized zirconia powder containing 5.28% by weight of $Y_2O_3$ and having a BET specific surface area of 18.7 m²/g and 400 g of zirconia balls having a diameter of 10 mm, were added thereto. The mixture was introduced into a vibration ball mill and subjected to wet pulverization treatment for one hour to obtain a zirconia slurry. The slurry concentration was 75.0% by weight, and the dispersant was used in an amount of 0.4% by weight relative to the partially stabilized zirconia. The apparent viscosity of the slurry was 0.73 poise at a shear rate of 10 sec$^{-1}$. By using this slurry, a slip casted product was obtained. This molded product had a cracking at the center.

TABLE 1

| | Example | | | | | | | | | | |
|---|---|---|---|---|---|---|---|---|---|---|---|
| | 1 | 2 | 3 | 4 | 5 | 6 | 7 | 8 | 9 | 10 | 11 |
| Production conditions | | | | | | | | | | | |
| Distilled water (g) | 30.3 | 27.1 | 24.7 | 24.7 | 24.6 | 24.6 | 24.5 | 32.0 | 32.0 | 32.0 | 32.0 |
| Slurry concentration (wt %) | 75.4 | 80.4 | 83.5 | 83.5 | 83.5 | 83.5 | 83.5 | 83.5 | 83.5 | 83.5 | 83.5 |
| 40% aqueous solution of dispersant (g) | 0.35 | 0.42 | 0.47 | 0.47 | 0.63 | 0.79 | 0.95 | 0.82 | 0.82 | 0.82 | 0.82 |
| Ratio of dispersant to partially stabilized zirconia (wt %) | 0.15 | 0.15 | 0.15 | 0.15 | 0.20 | 0.25 | 0.30 | 0.25 | 0.25 | 0.25 | 0.25 |
| Partially stabilized zirconia (g) | 93.4 | 112.4 | 126.2 | 126.2 | 126.2 | 126.2 | 126.2 | 164.1 | 164.1 | 164.1 | 164.1 |
| BET specific surface area of partially stabilized zirconia starting powder (m²/g) | 6.0 | 6.0 | 6.9 | 6.9 | 6.9 | 6.9 | 6.9 | 6.9 | 6.9 | 6.9 | 6.9 |
| Pulverization time by a ball mill (hr) | 1 | 1 | 1 | 1 | 1 | 1 | 1 | 1 | 1 | 1 | 1 |
| Pulvarization time by a rotary ball mill (hr) | 24 | 24 | 24 | 70 | 70 | 70 | 70 | 70 | 70 | 70 | 70 |
| Ratio of binder to partially stabilized zirconia (wt %) | 0.5 | 0.5 | 1.0 | 1.0 | 1.0 | 1.0 | 1.0 | 1.0 | 1.0 | 1.0 | 1.0 |
| Ratio of defoaming agent to partially stabilized zirconia (wt %) | 0.05 | 0.05 | 0.05 | 0.05 | 0.05 | 0.05 | 0.05 | 0.05 | 0.05 | 0.05 | 0.05 |
| Slurry concentration after addition of binder and defoaming agent (wt %) | 75 | 80 | 82.5 | 82.5 | 82.5 | 82.5 | 82.5 | 82.5 | 82.5 | 82.5 | 82.5 |
| Sintering temperature (°C.) | 1,500 | 1,500 | 1,500 | 1,500 | 1,500 | 1,500 | 1,500 | 1,250 | 1,350 | 1,350 | 1,500 |
| Sintering time (hr) | 2 | 2 | 2 | 2 | 2 | 2 | 2 | 24 | 2 | 24 | 2 |
| Results | | | | | | | | | | | |
| pH of wet pulverized slurry (poise) | 9.90 | 9.81 | — | 9.58 | 9.52 | 9.49 | 9.42 | 9.54 | 9.58 | 9.59 | 9.60 |
| Apparent viscosity of wet pulverized slurry (poiset) | 0.17 | 0.55 | — | 2.25 | 1.61 | 1.65 | 1.96 | 1.59 | 1.56 | 1.57 | 1.57 |
| BET surface area of partially | 6.8 | 7.0 | 7.1 | 10 | 9.9 | 9.9 | 9.8 | 9.5 | 9.5 | 9.5 | 9.5 |

TABLE 1-continued

| | Example | | | | | | | | | | |
|---|---|---|---|---|---|---|---|---|---|---|---|
| | 1 | 2 | 3 | 4 | 5 | 6 | 7 | 8 | 9 | 10 | 11 |
| stabilized zirconia after wet pulverization ($m^2/g$) Ratio of specific surface area of pulverized powder relative to starting powder (times) | 1.13 | 1.17 | 1.18 | 1.45 | 1.43 | 1.43 | 1.42 | 1.38 | 1.38 | 1.38 | 1.38 |
| Shrinkage of sintered body relative to the inner dimension of gypsum (mold) | 18.6 | 17.9 | 18.3 | 18.0 | 17.6 | 17.3 | 17.2 | — | — | — | — |
| Density of sintered body ($g/cm^3$) | 6.01 | 6.04 | 6.04 | 6.02 | 6.03 | 6.02 | 6.02 | 6.04 | 6.04 | 6.04 | 6.04 |
| Flexural strength of sintered body ($kgf/mm^2$) | 118 | 111 | 121 | 118 | 132 | 126 | 121 | 109 | 108 | 119 | 121 |
| Weibull coefficient | 30 | 26 | 20 | 11 | 25 | 22 | 19 | 13 | 13 | 21 | 25 |

EXAMPLE 12

Into a ball mill made of zirconia having an internal capacity of 250 ml, 24.6 g of distilled water and 0.63 g of an aqueous solution containing 40% by weight of ammoniuma polyacrylate, were charged and mixed. Then, 126.2 g of yttria partially stabilized zirconia and 400 g of zirconia balls having a diameter of 10 mm were added thereto. The mixture was subjected to wet pulverization treatment by a vibration ball mill and a rotary ball mill to obtain a zirconia slurry. To 135 g of this slurry, 2.68 g of a binder in a 42 wt % aqueous solution and 0.056 g of a defoaming agent were added, and the mixture was stirred at 30 minutes and defoamed under reduced pressure at 20 Torr for 20 minutes in a rotary evaporator. The slurry thus obtained was slip-casted into a cylindrical shape of 12 mm in diameter × 150 mm at 25° C. at room temperature. The molded product was dried at 25° C. for one day and machined into a cylindrical shape of 4.5 mm in diameter × 30 mm to obtain a zirconia shaped product.

Then, into a ball mill pot made of alumina having an internal capacity of 250 ml, 38.6 g of distilled water and 0.96 g of an aqueous solution containing 40% by weight of ammonium polyacrylate as a dispersant, were charged and mixed, and then 36.0 g of hydroxy apatite powder, 24.0 g of yttria partially stabilized zirconia powder and 400 g of zirconia balls having a diameter of 10 mm, were added thereto. The mixture was subjected to wet pulverization treatment by a vibration ball mill and a rotary ball mill to obtain a slurry mixture of hydroxyapatite and zirconia. To 93 g of this slurry, 13.3 g of a binder in a 42 wt % aqueous solution and 0.028 g of a defoaming agent and 213 g of distilled water were added. The mixture was stirred for 30 minutes and defoamed under reduced pressure of 20 Torr for 20 minutes in a rotary evaporator.

Into a 50 ml glass beaker, the slurry mixture of hydroxyapatite and zirconia was introduced. To this slurry, the above-mentioned machined zirconia shaped product was immersed in a length of 15 mm i.e. a half in the longitudinal direction, for 30 seconds to coat the powder mixture of hydroxy apatite and zirconia on the surface of the zirconia shaped product.

The coated product was dried at 25° C. for one day and at 90° C. for one day. Then, this dried product was heated in an electric furnace to 500° C. at a rate of 10° C./hr and maintained at 500° C. for one hour for degreasing. Then, the temperature was raised at a rate of 200° C./hr and sintered at 1,250° C. for 24 hours.

Thus, a ceramic implant comprising a sintered body of zirconia and a coating layer of a porous sintered body of a mixture comprising α-TCP and zirconia, formed on the surface of the sintered body of zirconia, was obtained.

EXAMPLE 13

Into a ball mill pot made of zirconia having an internal capacity of 250 ml, 24.6 g of distilled water and 0.63 g of an aqueous solution containing 40% by weight of ammonium polyacrylate were introduced and mixed, and then 126.2 g of yttria partially stabilized zirconia and 400 g of zirconia balls having a diameter of 10 mm, were added thereto. The mixture was subjected to wet pulverization treatment by a vibration ball mill and a rotary ball mill to obtain a zirconia slurry. To 135 g of this slurry, 2.68 g of a binder in a 42 wt % solution and 0.056 g of a defoaming agent were added, and the mixture was stirred for 30 minutes and defoamed under reduced pressure at 20 Torr for 20 minutes in a rotary evaporator. This slurry was slip-casted into a cylindrical shape of 12 mm in diameter × 150 mm at room temperature of 25° C. This molded product was dried at 25° C. for one day and machined into a cylindrical shape of 4.5 mm in diameter × 30 mm to obtain a zirconia shaped product.

Then, into a ball mill made of alumina and having an internal capacity of 250 ml, 38.6 g of distilled water and 0.96 g of an aqueous solution containing 40% by weight of ammoniuma polyacrylate, were introduced and mixed, and then 36.0 g of hydroxyapatite powder and 24.0 g of yttria partially stabilized zirconia powder and 400 g of zirconia balls having an diameter of 10 mm, were aded thereto. The mixture was subjected to wet pulverization treatment by a vibration ball mill and a rotary ball mill to obtain a slurry mixture of hydroxyapatite and zirconia. To 93 g of this slurry, 13.3 g of a binder in a 42 wt % aqueous solution and 0.028 g of a defoaming agent and 213 g of distilled water were added, and the mixture was stirred for 30 minutes and defoamed under reduced pressure at 20 Torr for 20 minutes in a rotary evaporator.

Into a 50 ml glass beaker, the slurry mixture of hydroxyapatite and zirconia was introduced. To this slurry, the above-mentioned machined zirconia shaped product was immersed in a length of 15 mm i.e. a half in the longitudinal direction, for 30 seconds to coat the powder mixture of hydroxyapatite and zirconia on the surface of the zirconia shaped product.

The coated product was dried at 25° C. for one day and at 90° C. for one day. Further, the dried product was heated in an electric furnace to 500° C. at a rate of 10° C./hr and maintained at 500° C. for one hour for degreasing. Then, the temperature was raised at a rate of 200° C./hr, and sintering was conducted at 1,250° C. for 24 hours.

Thus, the sintered product was subjected to hydrothermal treatment at 100° C. for 24 hours.

Thus, a ceramic implant comprising a sintered body of zirconia and a coating layer of a porous sintered body of a mixture comprising hydroxyapatite and zirconia, formed on the surface of the sintered body of zirconia, was obtained.

According to the above-mentioned process, it is possible to readily obtain a ceramic implant having high mechanical strength, which is free from breakage in a living body and has a surface porous layer firmly bonded to the core material and which has a biological activity. Thus, it is useful as an implant material for a living body such as an artificial tooth root, an artificial joint or an artificial bone.

We claim:

1. A ceramic implant comprising a sintered body of zirconia and a coating layer of a porous sintered body of a mixture comprising α-tricalcium phosphate and zirconia, formed on the surface of the sintered body of zirconia.

2. The ceramic implant according to claim 1 wherein the weight ratio of zirconia to α-tricalcium phosphate is within the range of from 0.05–20.

3. The ceramic implant according to claim 1 wherein the weight ratio of zirconia to α-tricalcium phosphate is within the range of from 0.1–2.5.

4. The ceramic implant according to claim 1 wherein the sintered body of zirconia has a flexural strength of at least 100 kgf/mm$^2$ and a Weibull coefficient of at least 10.

5. The ceramic implant according to claim 1 wherein the sintered body of zirconia has a flexural strength of at least 120 kgf/mm$^2$ and a Weibull coefficient of at least 15.

6. The ceramic implant according to claim 2 wherein the sintered body of zirconia has a flexural strength of at least 100 kgf/mm$^2$ and a Weibull coefficient of at least 10.

7. The ceramic implant according to claim 3 wherein the sintered body of zirconia has a flexural strength of at least 120 kgf/mm$^2$ and a Weibull coefficient of at least 15.

* * * * *